United States Patent [19]
Oberhardt

[11] Patent Number: 5,670,329
[45] Date of Patent: Sep. 23, 1997

[54] METHOD AND ANALYTICAL SYSTEM FOR PERFORMING FIBRINOGEN ASSAYS ACCURATELY, RAPIDLY AND SIMPLY USING A ROTATING MAGNETIC FIELD

[75] Inventor: Bruce J. Oberhardt, Raleigh, N.C.

[73] Assignee: Cardiovascular Diagnostics, Inc., Research Triangle Park, N.C.

[21] Appl. No.: 68,855

[22] Filed: May 28, 1993

[51] Int. Cl.$^6$ .............................. C12Q 1/56; G01N 31/22
[52] U.S. Cl. .............................. 435/13; 422/58; 422/61; 422/73
[58] Field of Search .............................. 73/54.31, 864.72; 209/212–215; 356/39; 364/413.09; 422/57, 58, 61, 73, 292; 435/13, 305, 805, 810, 969, 970; 436/69, 807

[56] References Cited

U.S. PATENT DOCUMENTS

| | | | |
|---|---|---|---|
| 3,861,197 | 1/1975 | Adler | 73/54.31 |
| 4,756,884 | 7/1988 | Hillman et al. | 422/73 |
| 4,849,340 | 7/1989 | Oberhardt | 435/13 |
| 5,110,727 | 5/1992 | Oberhardt | 435/13 |
| 5,120,834 | 6/1992 | Gargan et al. | 530/388.25 |
| 5,156,974 | 10/1992 | Grossman et al. | 436/69 |

FOREIGN PATENT DOCUMENTS

| | | |
|---|---|---|
| 47981/72 | 10/1972 | Australia . |
| 47981 | 4/1974 | Australia . |

OTHER PUBLICATIONS

"American Biogenetic Sciences, Inc. Initiates Clinical Trials [of] MH–1 For Imaging Blood Clots in the Lungs and Heart"; American Biogenetic Sciences, Inc. Press Release; Apr. 22, 1993.

"American Biogenetic Sciences, Inc. Receives U.S. Patent"; arron's; Jun. 15, 1992.

"American Biogenetic Sciences, Inc. Receives U.S. Patent [for] Blood Clot Detection Antibody"; American Biogenetic Sciences, Inc. Press Release; Jun. 1, 1992.

"A Six Year Prospective Study of Fibrinogen and Other Risk Factors Associated with Mortality in Stable Claudicants"; A.K. Banerjee, et. al.; Thrombosis and Haemostasis; 1992; pp. 261–263.

"American Biogenetic Sciences Signs License Agreement With Yamanouchi Pharmaceutical"; American Biogenetic Sciences, Inc. Press Release; Jan. 27, 1992.

"American Biogenetic Sciences, Inc. Fibrinogen Antibody Patent No. 5,091,512 Issued"; American Biogenetic Sciences, Inc. Press Release; Feb. 25, 1992.

"American Biogenetic Sciences, Inc. Fibrinogen Antibody Patent Allowed"; American Biogenetic Sciences, Inc. Press Release; Nov. 12, 1991.

"Exploration of rapid bedside monitoring of coagulation and fibrinolysis parameters during thrombolytic therapy"; D.C. Sane, et al; Blood Coagulation and Fibrinolysis, vol. 3; 1992; pp. 105–115.

"Clot Spotter Does a test for fibrinogen predict risk of heart disease?"; Scientific American; Jun., 1991.

"Clot Factors' CAD Role Emerging"; Patricia Thomas; Medical World News; May, 1991; p. 49.

"Dry Reagent Technology for Rapid, Convenient Measurements of Blood Coagulation and Fibrinolysis"; Bruce J. Oberhardt, et al.; Clinical Chemistry; vol. 37, No. 4; 1991; pp. 520–526.

(List continued on next page.)

Primary Examiner—Ralph Gitomer
Attorney, Agent, or Firm—Oblon, Spivak, McClelland, Maier & Neustadt, P.C.

[57] ABSTRACT

A method of performing a quantitative fibrinogen assay is provided which uses a dry reagent chemistry in combination with a rotational magnetic field and which has excellent correlation with the Fibrometer, the gold standard in the industry. Additionally, an apparatus for conducting the assay, a qualitative fibrinogen assay and a method for preparing a calibration curve for use with the quantitative fibrinogen assay are provided.

26 Claims, 5 Drawing Sheets

OTHER PUBLICATIONS

"Hemostasis and Thrombosis in the Clinical Laboratory"; Edited by Donna M. Corriveau, et al; 1988.

"Fibrinogen and Risk of Cardiovascular Disease"; William B. Kannel, et al; JAMA, vol. 258, No. 9; Sep. 4, 1987; pp. 1183–1186.

"Fibrinogen as a major risk factor in cardiovascular disease"; Nigel S. Cook, et al; *Trends in Pharmacological Sciences;* 1990.

"Procedures for the Coagulation Laboratory"; Douglas A. Triplett, et al; Educational Products Divison, American Society of Clinical Pathologists; 1981.

"Atherosclerotic Cardiovascular Disease, Hemostasis, and Endothelial Function"; Edited by Robert Boyer Francis, Jr. No Date Available.

Sane D.C. Exploration of Rapid Bedside Monitoring of Coagulation and Fibrinolysis Parameters During Thrombolytic Therapy. Blood oagulation and Fibrinolysis, vol. 3 1992 pp. 105–115.

METHOD AND ANALYTICAL SYSTEM FOR PERFORMING FIBRINOGEN ASSAYS ACCURATELY, RAPIDLY AND SIMPLY USING A ROTATING MAGNETIC FIELD

BACKGROUND OF THE INVENTION

1. Field of the Invention:

The present invention relates to improved methods and to improved analytical systems for performing fibrinogen assays.

2. Discussion of the Background:

Blood clotting reactions employed as clinical assays typically measure the time required for the formation of a fibrin clot. Blood clotting assays are principally used for screening, diagnosing, and monitoring patients receiving anticoagulant therapy.

There are many types of coagulation assays. These include: prothrombin time (PT); partial thromboplastin time (PTT); activated partial thromboplastin time (APTT); fibrinogen assay (i.e., the measurement of the concentration of clottable fibrinogen in a sample); thrombin time, also known as thrombin clotting time (TCT); activated clotting time (ACT); etc. The most frequently performed of these assays is prothrombin time.

The determination of the concentration of clottable fibrinogen in plasma is important for the investigation of coagulation disturbances in patients. Both immunological methods and coagulation tests have been used for the determination of fibrinogen. The immunological methods display severe diagnostic disadvantages have consequently not achieved practical importance.

In coagulation tests, the fibrinogen content is determined by the time required for coagulum formation. The most important of these methods is the method of Clauss (see Acta Haemat. 1957 17: 237–246).

In the Clauss method, a diluted plasma, i.e., a weak fibrinogen solution, is mixed with a concentrated thrombin solution, the amount of thrombin being about 100 U ml$^{-1}$ of plasma. Typically, 2 volumes of diluted sample containing fibrinogen are added to one volume of concentrated thrombin solution at 100 U/ml. With the help of a calibration curve, the fibrinogen content of the sample is correlated to the time taken for the visible appearance of a coagulum. Coagulation tests in which one records photometrically the formation of turbidity during the course of coagulation are also known. See, e.g., Ratge et al. (Clin. Chem. 1987 33(3):420).

Finally, quantitative methods are also known in which the coagulum formed is isolated and its protein content determined. In this approach, the sample is reacted with thrombin, and the coagulum is formed isolated, washed and then dried. The protein content of the coagulum or its weight is then determined.

Levine et al. U.S. Pat. No. 5,137,832 disclose a method for quantification of fibrinogen in a whole blood sample by centrifugation, heating, and recentrifugation to layer a band of fibrinogen-rich solution on top of a float contained in a tube.

Becker et al. U.S. Pat. No. 4,692,406 disclose a method for the simultaneous determination of fibrinogen and of fibrinogen fission product in plasma. This method uses a snake venom enzyme with thrombin-like activity. In this method, the period of time between the addition of the enzyme and commencement of turbidity formation, which is a measure of the amount of fibrinogen fission products, is measured. The speed of turbidity formation is subsequently measured to determine the amount of fibrinogen present in the sample.

The prothrombin time test and the activated partial thromboplastin time test are each commonly used clinical tests to determine a patient's ability to form clots. These tests, and the other tests noted above, are extensively used by hospitals, clinics, and laboratories for preoperative evaluations and for anticoagulant therapy administered to cardiac patients, among other patients. These tests are each based upon time measurements and, for the most part, measure what is called an endpoint or clotting time, which occurs when fibrinogen is being polymerized to fibrin.

Many of these types of assays monitor change in sample optical density to measure the reaction. See, for example, Natelson et al. (Am. J. Clin. Path. 1974 61 (6):828–833), Lipscomb (U.S. Pat. No. 4,720,787), Saito et al. (U.S. Pat. No. 4,217,107), Baughman et al. (U.S. Pat. No. 4,289,498), Gross et al. (U.S. Pat. No. 3,458,287), Eichelberger et al. (U.S. Pat. No. 4,047,890), Becker et al. (U.S. Pat. No. 4,692,406), Callahan et al. ("Semiquantitative Fibrinogen Determination from the PT Clotting Reaction," Tech. Bulletin THR8804, copyright 1988 by Organon Teknika, Durham, N.C., USA), and Carroll et al. ("The Clot Signature and New Aspects in Coagulation Testing," July 1989, Ortho Diagnostic Systems Inc., Raritan, N.J.).

In addition to being assayed by the coagulation rate as in the Clauss method noted above, fibrinogen can be assayed by the coagulation rate as in the Clauss method modified by Vermylen et al. (Clin. Chem. Acta 1963 8: 418–24), by sulfite precipitation, Rampling et al. (Clin. Chem. Acta 1976 67: 43), by the total coagulable fibrinogen method of Ratnoff et al. (J. Lab. Clin. Med. 1951 37: 316–320), or by an assay system based on the turbidity rate measurement of the conversion of fibrinogen to fibrin polymer sold by Du Pont (Du Pont Aca™, Du Pont Clinical Systems, Wilmington, Del., USA). The Vermylen et al. method uses a glass hook or platinum loop which is continuously moved in and out of the clotting mixture until the appearance of a fibrin web as the endpoint.

With many existing prior art methods for fibrinogen determination, centrifugation of the blood is necessary before performing the assay because the blood cells interfere with the measurement. Separation of the blood cells takes time and increases the overall time required for the assay. If a fibrinogen assay can be performed as soon as the blood is collected, in vitro artifacts which arise from plasmin activation (due to the action of thrombolytic drugs) should minimally, if at all, affect test results. For blood samples obtained from thrombolytic therapy patients, delays of even several minutes (currently ten to fifteen minutes with existing methods) could produce inaccurate results. One solution to this problem has been to use inhibitors of plasmin or plasminogen activator as an additive to the blood collection tube to preserve the sample prior to testing. The use of inhibitors, however, adds additional expense and also restricts the field of functional assays that may be performed subsequently on the sample.

Fibrinogen is an important indicator of bleeding risk. In thrombolytic therapy patients and other patients at risk for bleeding, it is not possible to obtain rapid fibrinogen determinations due to the long turnaround times in the hospital laboratory. Blood must first be obtained from the patient, transported to the laboratory, centrifuged and brought to the fibrinogen analyzer, which often must first be calibrated before the sample can be measured. When the sample is tested, the result must be sent to the physician. Rapid fibrinogen determination, as could be performed with a dry chemistry system, has not previously been achieved.

More than 50% of the deaths in the United States are due to a single thrombotic event—a blood clot in the vasculature of the heart, the brain, or the lungs, or complications resulting from deep venous thrombosis or peripheral vessel thrombosis. In addition to thrombotic-related deaths, a significant number of fatalities result from uncontrolled internal bleeding. Fibrinogen is an important protein, for it is the substance from which thrombi or clots are made. Excessive fibrinogen may predispose a patient to thrombosis. Insufficient fibrinogen may lead to spontaneous hemorrhage. Fibrinogen levels may become altered in a number of medical disorders, such as liver failure, sepsis, and disseminated intravascular coagulation, as well as during certain surgical procedures. The advent of modern therapeutic modalities, such as thrombolytic therapy and open heart surgery, has led to sudden iatrogenic decreases in patients' fibrinogen levels. In addition, the fibrinogen level may become suddenly increased as an acute phase reactant in myocardial infarction. In fact, a number of clinical studies have shown that fibrinogen level is a significant risk factor for ischemic heart disease and stroke in patients with cardiovascular disease, even more so than cholesterol. See, e.g., Banerjee et al. *Thromb. Haemostas*, 1992, 68: 261–263 and Meade in "Atherosclerotic Cardiovascular Disease, Hemostasis and Endothelial Function," ed. by R. B. Francis, Jr., Marcel Dekker, Inc., NY (1992). For these and other reasons, it has been an unfulfilled wish in medicine for many years to have a rapid, convenient fibrinogen assay which could be brought to the patient's bedside or near the patient for testing.

During the latter part of the twentieth century, a semi-automated laboratory analyzer for assaying clottable fibrinogen, known as the Fibrometer®, has been the "gold standard" in most clinical laboratories. This analyzer is very precise and employs the Clauss methodology. The Fibrometer is, however, not suitable for bedside or point-of-care use. This is because the instrument requires calibration on a frequent basis, is labor intensive, and is not portable. Furthermore, the probe is invasive, dipping into the sample and requiring cleaning after each sampling. The Fibrometer methodology also requires reconstitution of reagents. This reagent preparation phase takes additional time and requires accurate pipetting. Typically, users of this method batch all samples and run the system once a day, making rapid turnaround of test results even less likely.

Oberhardt and Gresalfi (U.S. Ser. No. 07/550,570) have taught the use of dry chemistry reagents incorporating magnetic particles to measure fibrinogen in a blood sample. This methodology, however, produces results which typically correlate with the Fibrometer results with a Pearson Correlation Coefficient (r) value of approximately 0.85. Until the present invention, this level of correlation is as good as may be obtained between two disparate fibrinogen methods, such as the modified Clauss and sulfite precipitation methods. See, e.g., Stump et al. (*Thromb Haemostas* 1988 59: 133–137).

However, since the Fibrometer is the current laboratory gold standard, it is desirable that a testing method for use near the patient (and away from the central laboratory) correlate extremely well with the Fibrometer, since it is still the method of choice in most laboratories.

SUMMARY OF THE INVENTION

Accordingly, it is an object of this invention to provide a simple and accurate method, and an analytical system, for performing a fibrinogen assay which does not suffer from the disadvantages noted above.

It is another object of this invention to provide a method, and an analytical system, for performing a fibrinogen assay requiring no preparation of a reagent-containing solution.

It is another object of this invention to provide a method, and an analytical system, for performing a fibrinogen assay which minimizes problems associated with reagent instability.

It is another object of this invention to provide a method, and an analytical system, for performing a fibrinogen assay requiring only a very small amount of sample.

It is another object of this invention to provide a rapid, convenient method for measurement of fibrinogen in a blood or plasma sample which correlates closely with laboratory methods utilizing the Clauss methodology and semi-automated mechanical or electro-mechanical clot detection systems, such as the Fibrometer.

Surprisingly, all of these objects, and other objects which will become apparent from the description of the invention provided herein, have been satisfied by the discovery of a method of performing a fibrinogen assay, comprising:

(i) subjecting to a rotating magnetic field a reaction chamber containing a premeasured amount of a dry reagent matrix comprising thrombin and in which is embedded a plurality of magnetic particles distributed homogeneously therethrough;

(ii) contacting the dry reagent matrix with a volume of a diluted blood sample sufficient to fill the reaction chamber, thereby freeing the magnetic particles to move under the influence of the rotating magnetic field;

(iii) optically monitoring the response of the magnetic particles to the rotating magnetic field, during clotting of the blood sample, to generate a response curve;

(iv) determining a clotting time endpoint from the response curve; and (v) comparing the clotting time endpoint from step (iv) to a stored standard calibration curve relating clotting time endpoint to fibrinogen content prepared in accordance with steps (i)–(iv) with samples of known fibrinogen content, to provide the amount of clottable fibrinogen in the sample.

In an additional embodiment is provided a system for performing the above fibrinogen assay comprising:

(i) a reaction slide bearing a sample well for receiving a liquid sample and a reaction chamber containing a dry reagent matrix in which is embedded a plurality of magnetic particles distributed homogeneously therethrough and a reagent comprising thrombin, the sample well and reaction chamber being in fluid connection through a transport zone of geometry such that a volume of liquid analyte sample placed in the sample well and corresponding to the volume of the reaction chamber is transported from the sample well to the reaction chamber;

(ii) a means for generating a rotating magnetic field; and (iii) an optical detection means for detecting the response of the magnetic particles to the rotating magnetic field.

BRIEF DESCRIPTION OF THE FIGURES

A more complete appreciation of the present invention and many of the attendant advantages thereof will be readily obtained as the same becomes better understood by reference to the following detailed description when considered in connection with the accompanying figures, wherein like reference numerals designate identical or corresponding parts throughout the several views.

DETAILED DESCRIPTION OF THE PREFERRED EMBODIMENTS

Figure 1:
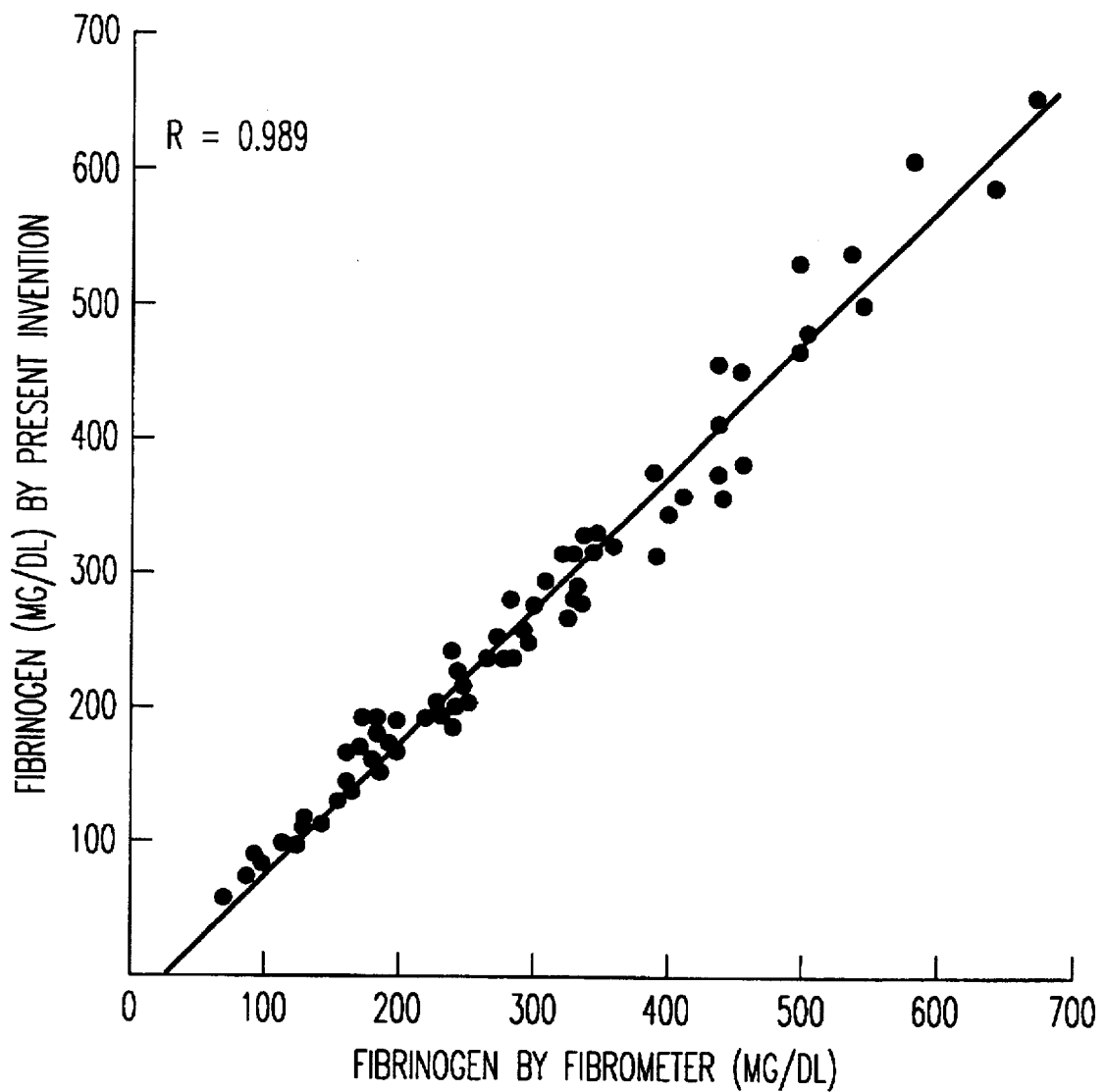
FIG. 1 illustrates the correlation of the method of the present invention with the laboratory "gold standard" Fibrometer.

The present invention relates to an improved method for performing a fibrinogen assay, comprising:

(i) subjecting to a rotating magnetic field a reaction chamber containing a dry reagent matrix in which is embedded a plurality of magnetic particles distributed homogeneously therethrough and a reagent comprising thrombin;

(ii) contacting said dry reagent matrix with a diluted blood sample, thereby freeing said magnetic particles to move under the influence of the rotating magnetic field;

(iii) optically monitoring the response of said magnetic particles to said rotating magnetic field, during clotting of said blood sample, to generate a response curve;

(iv) determining a clotting time endpoint from said response curve;

(v) comparing the clotting time endpoint from step (iv) to a stored standard calibration curve relating clotting time endpoint to fibrinogen content prepared in accordance with steps (i)–(iv) with samples of known fibrinogen content, to provide the amount of clottable fibrinogen in the sample.

The dry reagent of the present invention contains thrombin as the reagent acting to induce fibrinogen conversion to fibrin monomer and subsequent polymerization. The thrombin of the present invention may include any thrombin effective to induce fibrinogen polymerization and is preferably selected from human thrombin, bovine thrombin and porcine thrombin, most preferably human thrombin or bovine thrombin.

The method of the present invention may use samples of whole blood or samples which are derived from blood, such as plasma. To perform a fibrinogen assay with the present invention, it is necessary to first dilute the sample with a suitable diluent. This is preferably and simply achieved by utilizing Owren's buffer, the standard for Clauss fibrinogen tests. A variety of buffers, however, may be used. The dilution can range from 1 part sample in 5 parts buffer, for very low fibrinogen samples, to approximately 1 part sample in 20 parts buffer, for the highest levels encountered, with the dilution preferably being 1 part sample in 10 parts buffer. Other dilutions may be used but are needed only if the resulting clotting time is unreasonably long or unreasonably short.

Additionally, the diluted blood sample used in the present invention, either whole blood or plasma, may contain one or more anticoagulants, if desired. Suitable anticoagulants include conventional anticoagulants used in the art, such as citrate, low levels of heparin, and EDTA. Preferred among these is the use of citrate.

When whole blood is used in the method of the present invention, the blood fibrinogen concentration may be converted into plasma fibrinogen concentration by the use of a suitable algorithm which accounts for blood % cell fraction, or hematocrit. A suitable algorithm is as follows:

$$[\phi]_p = \frac{[\phi]_B}{1-(H/100)}$$

where:

[$\phi$]$_P$=concentration of fibrinogen in the plasma

[$\phi$]$_B$=concentration of fibrinogen in the blood

H=the % cell fraction in the sample (typically the hematocrit).

Prior methods for determining fibrinogen level require the frequent preparation of a calibration curve relating the clotting time to the fibrinogen content of the sample. The prior art methods require that this calibration curve be run for every sample or at least once for every group of 20–30 samples for accuracy. However, the present method allows for use of a stored calibration curve generated by the use of samples of known fibrinogen content in conjunction with the sample slide, rotating magnetic field and method of the present invention.

If the whole blood or plasma is used undiluted, and a lower concentration of thrombin is utilized in the dry reagent (1–5 units/ml), then instead of quantitatively measuring fibrinogen, the thrombin time or thrombin clotting time can be measured. Such a determination could be used as a screening test for abnormal fibrinogen concentration. For example, a normal fibrinogen concentration is considered to be 180–400 mg/dL. By using an undiluted sample, the thrombin clotting time measured can determine if the fibrinogen level of the sample falls within the normal range or outside of the normal range. Normal fibrinogen levels, as defined above, give thrombin times of from 10 to 13 seconds. Abnormal fibrinogen levels give thrombin times of greater than 13 seconds, sometimes greater than 20 seconds. However, use of an undiluted sample cannot be used to determine whether the fibrinogen level is too high or too low.

In a further embodiment of the present invention, the results obtained by the method of the present invention can be easily mapped onto local reference methods in order to have the results agree with the local reference method. For example, most hospitals have their own set of reference standards and values of fibrinogen which that hospital considers as "normal". Since the reference methods of two different hospitals may vary by 25–50 mg/dL, or more, using the same sample, it is advantageous to have the method of the present invention be flexible enough to account for this difference while using the same stored calibration curve prepared using the method of the present invention. This is done by mapping the results obtained using the method of the present invention onto the local reference method so that the values obtained can be interpreted by the particular hospital in question and correlate to the values obtained by that particular hospitals usual reference method. This mapping may be done in one of two ways: (1) by magnetically encoding the data mapping coordinates onto a magnetic strip on a test card containing the reaction slide of the present invention, or (2) by having the user reprogram the instrument measuring the response of the method of the present invention to report a mapped test result. The mapping method itself uses conventional data manipulation techniques to correlate the stored standard calibration curve of the present invention to the local reference method of the particular user.

While the assay of the present invention will work by simply using a premeasured amount of dry reagent containing magnetic particles on any solid surface, such as a microtiter plate or other substantially flat surface, a capillary slide geometry is ideally suited for creating a properly patterned format, housing the dry reagent and monitoring the sample. Suitable capillary slide geometries are slides such as those described in U.S. Pat. No. 4,849,340, U.S. Pat. No. 5,110,727, or U.S. patent application Ser. No. 08/018, 415, each to Oberhardt, which are hereby incorporated by reference.

A particularly preferred reaction slide can be prepared from a plastic laminate structure comprising a capillary reaction chamber with a vent opening adjacent to one end and a neck region tapering toward and opening into a sample well. While the reaction slide may be constructed to be any dimensions which provide capillary properties to the slide, a particularly preferred embodiment of the reaction slide has a 10×8×0.178 mm rectangular capillary reaction chamber with an 8×3 mm vent opening and a 9 mm neck region which tapers to 2 mm at the end of the neck region adjacent to a circular well of 6.5 mm diameter. The base of the preferred reaction slide is opaque, preferably white, with the cover and spacer being transparent. The reaction slide can be assembled using a spacer such as double sided adhesive plastic film. The base and cover are preferably 0.25 mm thick and the spacer is preferably 0.178 mm thick. The reaction slide is filled with the dry reagent matrix, containing magnetic particles, frozen, and subsequently lyophilized in a conventional freeze-dryer. When dried, the reaction slides can be packaged with desiccant and stored under refrigeration, preferably at 2°–8° C., until use.

The dry chemistry reaction slide of the present invention contains 20 to 100 units/ml of thrombin, with 50 units/ml of thrombin being preferred. The use of reagents other than thrombin, which induce the polymerization of fibrinogen, such as snake venom (Bothrops atrox or reptilase), is less desirable, because correlation with the thrombin based methods is generally on the order of 0.85 using the Pearson correlation coefficient (r) with some significant individual patient outliers. This result is readily verified using the Fibrometer to perform tests with both reptilase and thrombin reagents. Even the reptilase equivalent of the thrombin time yields somewhat different results and is called "reptilase time." If high correlation with the Fibrometer is desired using the present invention (i.e., r>0.95), it is therefore necessary to use a thrombin based reagent.

The dry reagent of the present invention further comprises magnetic particles which are interspersed substantially homogeneously therethrough. Suitable magnetic particles include those discussed in either of U.S. Pat. No. 4,849,340 or U.S. Pat. No. 5,110,727.

It is important that the dry reagent of the present invention be prepared such that it is rapidly dissolved upon the addition of the blood or blood-derived sample. Lyophilization on a surface, or even better, between two surfaces closely apposed at a capillary or near-capillary distance, such as in the above described reaction slide, works best. This produces a mass of low matter content which enables rapid sample penetration and dissolution. Lyophilization can be achieved using commercially available freeze drying apparatus.

Prior to lyophilization of the reagent, the capillary space of the reaction slide is filled with the reagent. Upon lyophilization, the resulting reagent may appear in at least two different forms. The first of these forms is "fluffy" in nature and completely fills the capillary space with holes or interstices within the "fluffy" reagent. The second form that the reagent can take is that of a film on the bottom of the capillary chamber with a headspace between the film and the top of the capillary chamber. While both of these forms work in the present invention, the second form, the reagent film, is particularly preferred because it is less fragile and unlikely to fracture upon subjecting the test card (reaction slide) to mechanical shock.

However, a third, intermediate form or "crystalline state" which extends from the bottom film of the reaction slide to the top in the form of "plates" gives the best precision (as low a coefficient of variation (cv) as 2%). This state is inbetween a film containing more moisture and a very dry powdery, fluffy state. Both of these states typically provide % cv values of 3–6. The crystalline state is achieved by freezing the liquid filled reaction slide at a temperature below −190° C. and subjecting the reaction slide to high vacuum for approximately 14 hours at −15° C. before warming to 25° C. This is achieved using a freeze drying apparatus.

Although freeze drying provides excellent results for preparation of the dry magnetic particle-containing reagent, room temperature, vacuum, desiccant, convective, or other drying means can also be used to achieve good results. For example, room temperature drying of reagent on the base of a reaction slide, with spacer in place, followed by attachment of the cover can be used to obtain a self-metering dry reagent containing element.

The magnetic particle movement caused by the rotational magnetic field used in the present method, can be measured by light scatter/reflectance. A light source, such as an infrared light emitting diode, is appropriately situated for providing incident light on the reaction chamber and a detector positioned for detecting light rays reflected or scattered from the sample within the reaction volume. The detector can be positioned at any location that will permit it to detect the reflected (scattered) rays, but a position between 90° and 10°, inclusively, from the plane of rotation of the magnetic field is preferable, with a position between 90° and 45° being more preferred. Placement of the detector at 90° from the plane of rotation of the magnetic field (perpendicular to the longest two dimensions of the capillary reaction chamber) is most preferred. The light source is preferably a light-emitting diode with a peak light output at approximately 930 nm situated so that the emitted light is preferably directed at the reaction slide at a 45° angle to its surface plane. The detector is preferably a photodiode having a filter with a peak at 920 nm±120 nm, which is situated normal to the reaction slide surface plane. The detector is connected to a signal reporting means. Suitable signal reporting means include a preamplifier and a chart recorder or a current voltage amplifier, 10-bit 200 sample/sec digitizer and computer.

Figure 5:
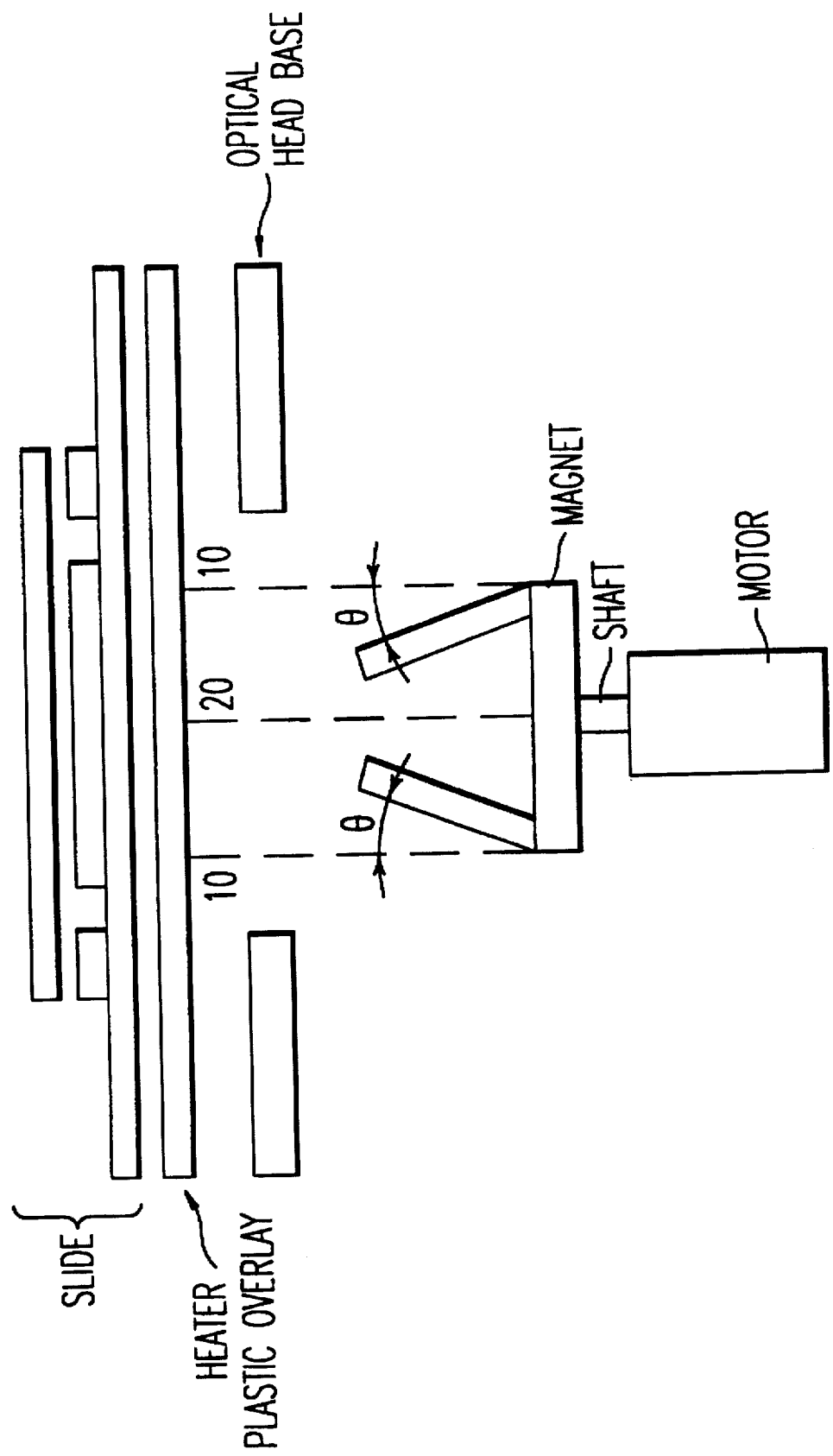
FIG. 5 shows a schematic of a magnet used to generate the rotational magnetic field of the present invention.

The rotating magnetic field used in the present invention may be generated by rotating a permanent magnet with pole pieces pointing in the same direction, such as a conventional U-shaped magnet, or which simultaneously point toward or away from the center line of the magnetic field produced by such a conventional U-shaped magnet. This is more readily understood by considering FIG. 5, which shows the configuration of a magnet which produces a suitable magnetic field upon rotation of the magnet. In FIG. 5, each pole piece forms an angle θ from lines 10 and 10' perpendicular to the plane of the reaction slide. In the method of the present invention, this angle θ is from −45° to +45°, with the pole pieces each pointing towards the center line 20 or away from the center line 20. Another suitable magnet for generating the rotating magnetic field of the present invention is a circular series of electromagnetic coils, which are arranged and activated in sequence to generate the rotating magnetic field. These coils can be wound around iron cores that are tied to a common point to create the equivalent of a rotating U-magnet when energized sequentially. In an assembly of this type, the iron cores would tilt inward at an angle ($\theta$, in FIG. 5) that could exceed 45°.

The rotating magnetic field is preferably generated by utilizing a U-shaped ALNICO magnet with two pole pieces facing the reaction slide. Alternatively, a combination of rare earth magnets may be utilized in conjunction with pole pieces and a base to achieve the equivalent of a U-shaped ALNICO magnet of suitable field strength but with less overall mass. This can be achieved using neodymium-iron-boron magnets, suitably mounted. The magnet for magnet assembly can be attached to the shaft of a D.C. motor via a hole drilled in the magnet's center, allowing it to spin about its axis. The pole pieces may be situated at any distance from the reaction chamber, containing the dry reagent of the present invention, that is sufficient to provide a rotating magnetic field active on the reaction chamber and its contents. The distance between the pole pieces of the magnet and the lower surface of the reaction slide base is preferably approximately 5 mm. The temperature of the reaction slide may be maintained at any temperature that allows unhindered movement of the magnetic particles after dissolution of the reagent (i.e., temperatures that do not effect freezing or denaturation of the reagent and the sample) and is preferably maintained at 37° C. with a suitable heating means, such as an electrical strip heater. When an electrical strip heater is used, the heater can be affixed to an aluminum plate, of approximately 0.04 in thickness, by means of a thermally stable adhesive, with the heater and plate assembly situated between the spinning magnet and reaction slide.

With this arrangement, blood coagulation reactions can be measured in the rotary shear field, since the coalescence of the suspended magnetic iron oxide particles and entrapment by polymerizing fibrin yields a rapid progressive decrease in the light scatter and absorption and consequently an increase in background reflectance from the reaction slide base.

Figure 4:
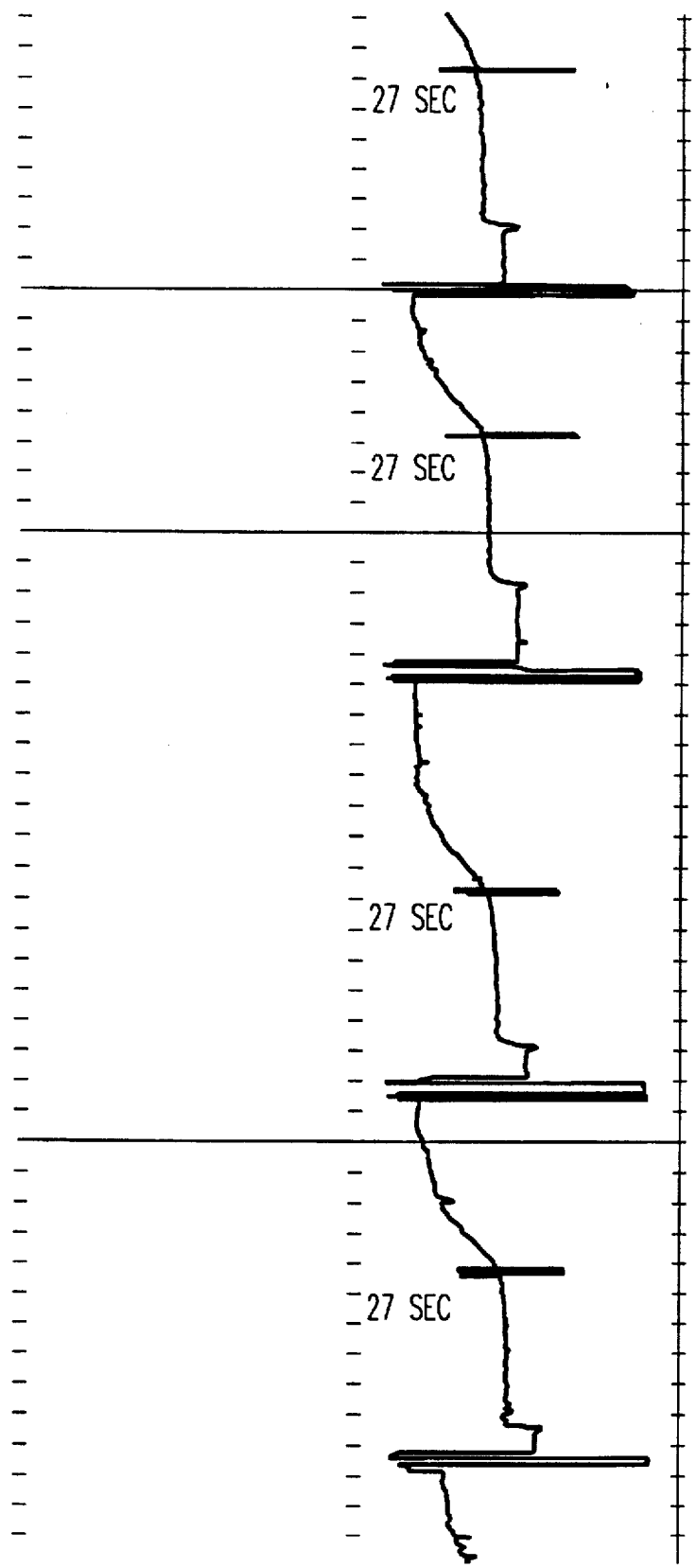
FIG. 4 shows typical raw data curves obtained using the instrument and dry chemistry reaction slide of the present invention.

The range of magnetic field rotational frequencies useful in the present invention is from approximately 15 to 60 Hz. The preferred rotational frequency of the magnet for best signal-to-noise ratios is approximately 35 Hz for diluted plasma samples and approximately 20 Hz for whole blood samples. The magnetic field, when the magnet is at rest, is preferably 420 gauss±20 gauss, parallel to the sample, and 0 gauss±50 gauss, perpendicular to the sample. The resultant endpoint (FIG. 4: rise after the long plateau region) may be detected in a variety of ways known to practitioners of the art of signal processing. In a preferred embodiment, the entire waveform is stored in computer memory and linear regressions performed for the plateau region and rising region, the intersection of these regression lines providing the end time or endpoint. Alternatively, the clotting time endpoint could be determined as a rise above a preset threshold from the signal amplitude established during the plateau. The endpoint is indicated in FIG. 4 as a downward reference line extending below the curve. This line is not part of the actual signal.

This arrangement is different from that taught in the prior art by Adler (U.S. Pat. No. 3,650,698) and Lichtenstein (Australian Application Number 47981/72 {460.038} {Dec. 13, 1971, USA, 207196}). Adler utilized a spinning bar or cylindrical magnet which tended to move the particles to the periphery of the mixing zone. In addition, the magnetic particles of Adler were entrapped in a polyvinyl pyrrolidone film in a spot on a surface without a capillary reaction chamber. Adler further required dispensing a precise aliquot of plasma onto the spot containing particles and required a preincubation period (e.g., 60 seconds) for the particles to properly suspend in the liquid. Afterward, a precise aliquot of liquid clotting reagent (thromboplastin), which was previously prepared in accordance with the manufacturer's instructions, was dispensed onto the spot containing sample and suspended particles. The timer was started at the moment that reagent was dispensed and stopped when the particles coalesced to produce a large change in reflectance. Adler did not teach the use of lyophilized coagulation reagent with magnetic particles essentially homogeneously dispersed therethrough, nor did he teach the use of a capillary reaction chamber. Therefore, the convenience to the user of the present invention could not be achieved. In addition, Adler did not teach the measurement of fibrinogen in a sample.

Lichtenstein considers fibrinogen measurement as a potential application of his apparatus but does not teach the methodology for achieving this objective. Moreover, the apparatus of Lichtenstein requires a stationary second magnet in addition to the spinning first magnet to achieve the mixing useful to the applications taught. The apparatus of Lichtenstein is considered merely as a refinement of the apparatus of Adler.

Having generally described this invention, a further understanding can be obtained by reference to certain specific examples which are provided herein for purposes of illustration only and are not intended to be limiting unless otherwise specified.

EXAMPLES

Example 1

Figure 2:
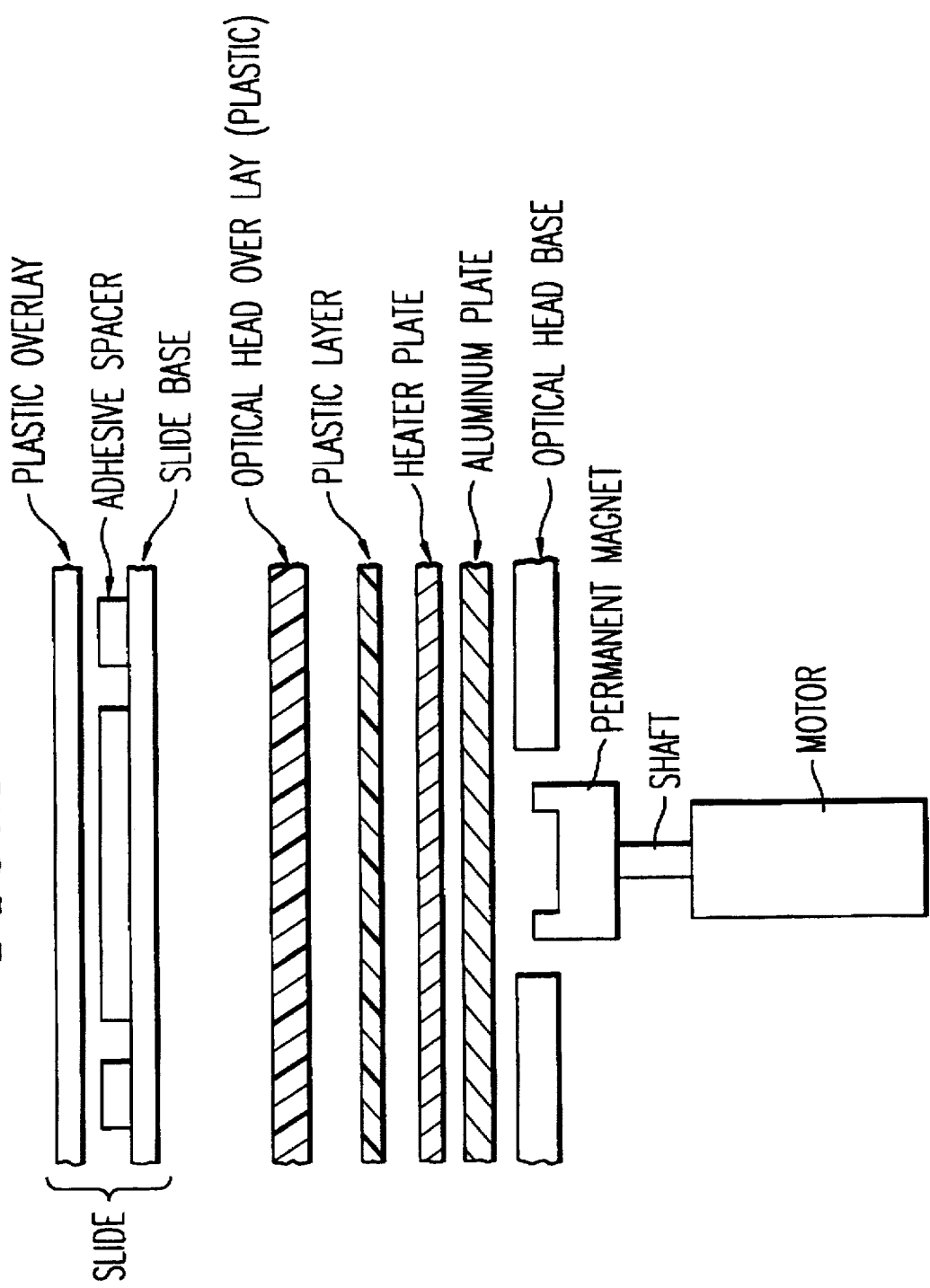
FIG. 2 is an exploded perspective of an assembled reaction slide and a means for generating a rotational magnetic field which can be used in the method of the present invention.
Figure 3:
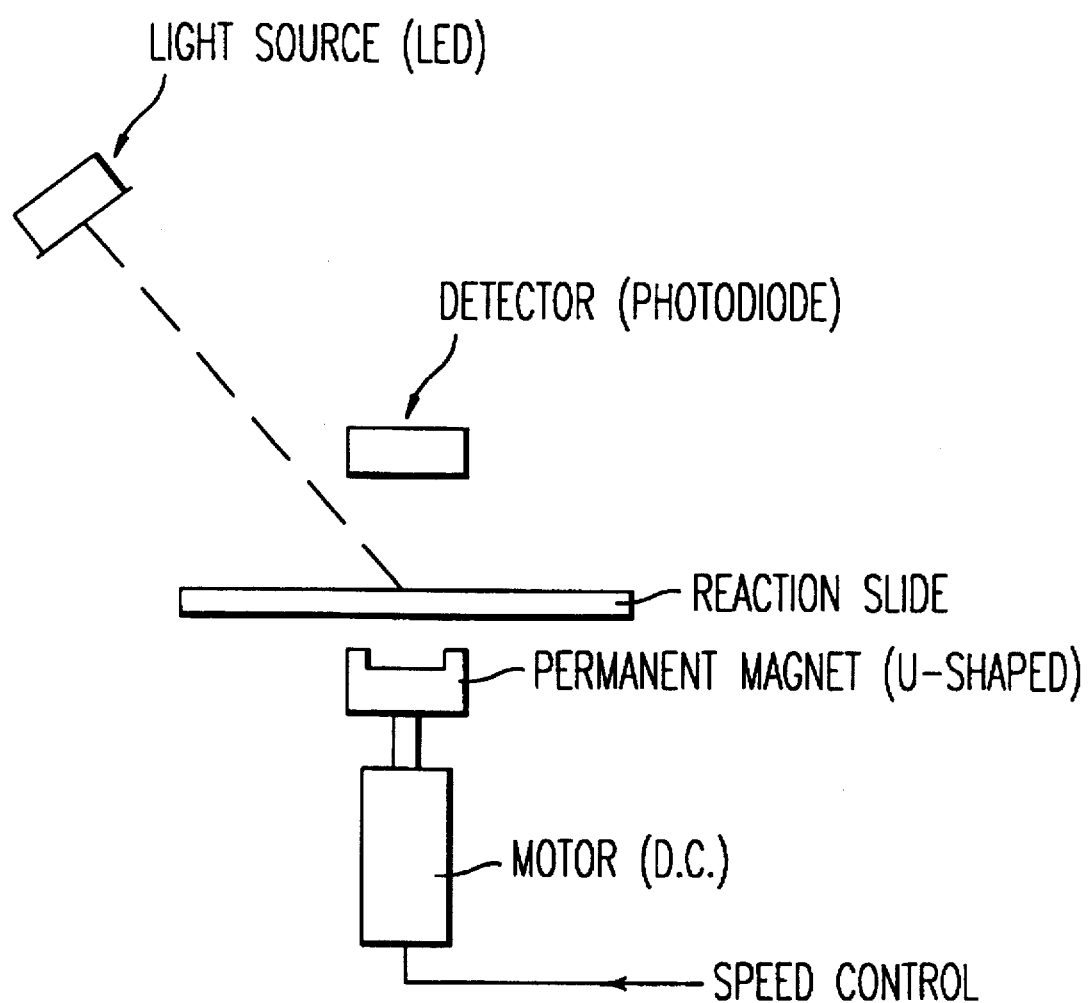
FIG. 3 is a graphical representation of an apparatus for use in the method of the present invention.

A dry chemistry reaction slide for measuring fibrinogen in a sample was prepared by placing a suspension of 7 mg/ml of $Fe_3O_4$ (magnetic iron oxide) of 0.3 micron average particle diameter in 0.1% bovine serum albumin (BSA) and bovine thrombin reagent Dade® Data-Fi® Thrombin Reagent, Baxter Diagnostics, Inc., Catalogue No. B4233-27, diluted to approximately 50 units/ml. The mixture was pipetted into the reaction volume of the reaction slide and followed by freezing at −195° C. in liquid nitrogen. The reaction slides prepared in this way were then lyophilized in a freeze dryer with an initial shelf temperature of −35° C. The resulting dried reaction slides were brought to room temperature and packaged in foil pouches until they were used for fibrinogen determination. The same thrombin reagent was utilized in liquid form at 50 units/ml concentration for fibrinogen assay of plasma samples using the Fibrometer coagulation instrument. For each instrument, calibration was performed using an assayed reference plasma (ARP), Helena Laboratories, Inc. The plasma samples were diluted in Owren's buffer and tested according to the Clauss methodology. FIG. 1 shows the results of the study performed in this example. When fibrinogen (mg/DL) obtained with the dry chemistry reaction slide and associated instrument (FIG. 2) was plotted at the ordinate versus fibrinogen obtained with the Fibrometer, a straight line resulted, having a Pearson correlation coefficient of r=0.989. The data shown in FIG. 1 consist of 76 hospital patients, 3 assayed reference plasmas (ARPs), and 2 pooled normal plasmas (PNPs). FIG. 3 shows typical raw data curves obtained with the instrument and dry chemistry reaction slide, indicating the precision of clotting time in repeated measurements.

Example 2

A dry chemistry reaction slide for assay of fibrinogen was prepared as in Example 1 and successfully tested using bovine thrombin reagent, Sigma Company Catalogue No. 4648.

Example 3

A dry chemistry reaction slide was prepared as in Example 1 and successfully tested using human thrombin reagent, Ortho Diagnostic Systems, Inc. Product Code 731200 (Fibrindex).

Example 4

A dry chemistry reaction slide was prepared as in Example 1, but 0.5% mannitol (Sigma Catalogue No. M-4125) was added to the reaction mixture as an additive prior to lyophilization. Results were comparable.

Example 5

A dry chemistry reaction slide was prepared as in Example 1, but 0.1% bovine serum albumin (BSA) was also used in the reaction mixture as an additive prior to lyophilization. The assay precision improved slightly. The addition of 20 mg/ml polyethylene glycol (PEG) prior to lyophilization shortened the clotting times and decreased assay precision.

Example 6

A dry chemistry reaction slide was prepared as in Example 2 utilizing, in addition, 50 mM HEPES buffer and 10 mg/ml mannitol. Good results were obtained.

Example 7

Test cards for thrombin time determination were prepared by combining 1.5/ml human thrombin, 50mM HEPES buffer, pH 7.3, 2 mg/ml polyethylene glycol (3400 dalton), 0.1 mg/ml polybrene and 1.0 mg/ml BSA with 7 mg/ml $Fe_3O_4$ of 0.3 micron average particle diameter. The mixture was pipetted into the reaction volume of the reaction slide and followed by freezing at −195° C. in liquid nitrogen. The reaction slides prepared in this way were then lyophilized in a freeze dryer with an initial shelf temperature of −35° C. The resulting dried reaction slides were brought to room temperature and packaged in foil pouches until they were used for thrombin time determination. For thrombin time testing, undiluted sample was utilized, and clotting time was measured. Normal fibrinogen levels (180–400 mg/dL) gave thrombin time values ranging between 10 and 13 seconds under these conditions. Abnormal fibrinogen levels resulted in thrombin time values greater than 13 seconds and sometimes greater than 20 seconds.

Example 8

Plasma samples with fibrinogen levels of approximately 120, 215, 219, and 360 mg/dL were tested, as in Example 1. These samples were first diluted. One aliquot of each of these diluted samples was warmed to 37° C. prior to addition of the sample to the sample well of the reaction slide. A second aliquot of each diluted sample was added at room temperature to the sample well. In all cases, the reaction chamber of the dry chemistry reaction slide was maintained at 37° C. The resultant correlations with the Fibrometer (with all samples pre-warmed at 37° C.) were r=0.999 for the 37° C. pre-warmed sample aliquots and r=0.999 for the room temperature (24° C.) sample aliquots, with mean values for each of the paired samples generally within the standard deviation for a single measurement. The temperature of the applied sample, thus, has little effect or correlation in this range.

Example 9

Five normal volunteer donors were tested by performing a skin puncture with an Autolet® device and collecting the blood in capillary tubes. For each donor, the blood sample in one capillary tube was expelled within one minute into a citrate containing buffer (3.2% buffered trisodium citrate anticoagulant) for a final 1:10 dilution, applied to the dry chemistry reaction slide of Example 5 (without PEG) and analyzed. Plasma fibrinogen was determined for the five donors by collecting venipuncture samples (9 volumes blood: 1 volume 3.2% citrate) in evacuated collection tubes, centrifuging to prepare platelet-poor plasma, and testing with the Fibrometer. The fibrinogen values ranged from approximately 230 to 380 mg/dL. The resulting data, even in this narrow range which would be expected to show much poorer correlation, showed an excellent correlation of 0.924 with plasma fibrinogen values obtained for the same donors with the Fibrometer using venipuncture samples. Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method of performing a quantitative fibrinogen assay, comprising:
   (i) contacting a dry reagent matrix, comprised of thrombin and in which is homogeneously embedded a plurality of magnetic particles, contained in a reaction chamber and subjected to a rotating magnetic field generated by a process comprising spinning a north pole and a south pole of a magnetic field about a central point, with an amount of a diluted blood sample sufficient to fill said reaction chamber, thereby freeing said magnetic particles to move under the influence of the rotating magnetic field;
   (ii) optically monitoring the response of said magnetic particles to said rotating magnetic field, during clotting of said blood sample, generating a response curve relating clotting time to fibrinogen concentration;
   (iii) determining a clotting time endpoint from said response curve; and
   (iv) comparing the clotting time endpoint from step (iii) to a stored standard calibration curve relating clotting time endpoint to fibrinogen content, prepared with samples of known fibrinogen content, to determine the amount of clottable fibrinogen in the sample.

2. A method of performing a fibrinogen assay according to claim 1, wherein said thrombin is human thrombin.

3. A method of performing a fibrinogen assay according to claim 1, wherein said thrombin is bovine thrombin.

4. A method of performing a fibrinogen assay according to claim 1, wherein said diluted blood sample is diluted whole blood.

5. A method of performing a fibrinogen assay according to claim 1, wherein said diluted blood sample is diluted plasma.

6. A method of performing a fibrinogen assay according to claim 4, wherein said diluted whole blood further comprises an anticoagulant.

7. An apparatus for performing a fibrinogen assay comprising:
   (i) a reaction slide bearing a sample well for receiving a liquid sample and a reaction chamber containing a dry reagent matrix comprising thrombin and in which is embedded a plurality of magnetic particles distributed homogeneously therethrough, said sample well and reaction chamber being in fluid connection through a transport zone of geometry such that a volume of liquid analyte sample placed in said sample well and corresponding to the volume of said reaction chamber is transported from said sample well to said reaction chamber;

(ii) providing a rotating magnetic field generated by a process comprising spinning a north pole and a south pole of a magnetic field about a central point (iii) an optical detection means for detecting a response of said magnetic particles to said rotating magnetic field.

8. An apparatus for performing a fibrinogen assay according to claim 7, wherein said thrombin is human thrombin.

9. An apparatus for performing a fibrinogen assay according to claim 7, wherein said thrombin is bovine thrombin.

10. An apparatus for performing a fibrinogen assay according to claim 7, wherein said diluted blood sample is diluted whole blood.

11. An apparatus for performing a fibrinogen assay according to claim 10, wherein said diluted whole blood further comprises an anticoagulant.

12. An apparatus for performing a fibrinogen assay according to claim 10, further comprising a calibration curve storage means.

13. An apparatus for performing a fibrinogen assay according to claim 7, wherein said diluted blood sample is diluted plasma.

14. A method of performing a thrombin clotting time test, comprising:

(i) contacting a dry reagent matrix comprised of thrombin and in which is homogeneously embedded a plurality of magnetic particles, contained in a reaction chamber and subjected to a rotating magnetic field generated by a process comprising spinning a north pole and a south pole of a magnetic field about a central point, with an amount of an undiluted blood sample sufficient to fill said reaction chamber, thereby freeing said magnetic particles to move under the influence of the rotating magnetic field;

(ii) optically monitoring the response of said magnetic particles to said rotating magnetic field, during clotting of said blood sample, to generate a response curve; and (iii) determining a thrombin clotting time from said response curve.

15. A method of performing a thrombin clotting time test according to claim 14, wherein said thrombin is human thrombin.

16. A method of performing a thrombin clotting time test according to claim 14, wherein said thrombin is bovine thrombin.

17. A method of performing a thrombin clotting time test according to claim 14, wherein said undiluted blood sample is undiluted whole blood.

18. A method of performing a thrombin clotting time test according to claim 17, wherein said undiluted whole blood further comprises an anticoagulant.

19. A method of performing a thrombin clotting time test according to claim 14, wherein said undiluted blood sample is undiluted plasma.

20. A method for preparing a standard calibration curve for measurement of fibrinogen, comprising:

(i) contacting a dry reagent matrix comprised of thrombin in which is homogeneously embedded a plurality of magnetic particles, contained in a reaction chamber and subjected to a rotating magnetic field generated by a process comprising spinning a north pole and a south pole of a magnetic field about a central point, with an amount of a diluted reference sample sufficient to fill said reaction chamber, wherein said diluted reference sample contains a known quantity of fibrinogen, thereby freeing said magnetic particles to move under the influence of the rotating magnetic field;

(ii) optically monitoring the response of said magnetic particles to said rotating magnetic field, during clotting of said reference sample, to generate a response curve;

(iii) determining a clotting time endpoint from said response curve;

(iv) repeating steps (i)–(iii) using for each clotting time determination another diluted reference sample having a known quantity of fibrinogen, wherein each additional diluted reference sample used has a different known quantity of fibrinogen from all other diluted reference samples used; and (v) plotting the clotting time endpoint for each sample on one axis of a two-dimensional plot, with the other axis being the quantity of fibrinogen in the blood samples used in steps (i)–(iv) or storing electronically data comprising said clotting time endpoint for each sample and said quantity of fibrinogen in said samples, to generate said two-dimensional plot and generating said two-dimensional plot from said electronically stored data.

21. A method for preparing a standard calibration curve for measurement of fibrinogen according to claim 20, wherein said thrombin is human thrombin.

22. A method for preparing a standard calibration curve for measurement of fibrinogen according to claim 20, wherein said thrombin is bovine thrombin.

23. A method for preparing a standard calibration curve for measurement of fibrinogen according to claim 20, wherein said diluted reference sample is diluted whole blood.

24. A method for preparing a standard calibration curve for measurement of fibrinogen according to claim 23, wherein said diluted whole blood further comprises an anticoagulant.

25. A method for preparing a standard calibration curve for measurement of fibrinogen according to claim 20, wherein said diluted reference sample is diluted plasma.

26. A method of performing a quantitative fibrinogen assay, comprising:

(i) contacting a dry reagent matrix, comprised of thrombin and in which is homogeneously embedded a plurality of magnetic particles, contained in a reaction chamber and subjected to a rotating magnetic field substantially identical to a magnetic field generated by rotating, about a central axis, a permanent magnet having opposite pole pieces, wherein the opposite pole pieces point parallel in the same direction or point simultaneously toward or away from said central axis by an angle, θ, of from −45° to +45° relative to a line extending perpendicular from said reaction slide;

with an amount of a diluted blood sample sufficient to fill said reaction chamber, thereby freeing said magnetic particles to move under the influence of the rotating magnetic field;

(ii) optically monitoring the response of said magnetic particles to said rotating magnetic field, during clotting of said blood sample, generating a response curve relating clotting time to fibrinogen concentration;

(iii) determining a clotting time endpoint from said response curve; and (iv) comparing the clotting time endpoint from step (iii) to a stored standard calibration curve relating clotting time endpoint to fibrinogen content, prepared with samples of known fibrinogen content, to determine the amount of clottable fibrinogen in the sample.

* * * * *